United States Patent [19]
Givens et al.

[11] Patent Number: 5,708,591
[45] Date of Patent: Jan. 13, 1998

[54] METHOD AND APPARATUS FOR PREDICTING THE PRESENCE OF CONGENITAL AND ACQUIRED IMBALANCES AND THERAPEUTIC CONDITIONS

[75] Inventors: Thomas B. Givens, Rougemont; Paul Braun, Durham; Timothy J. Fischer, Raleigh, all of N.C.

[73] Assignee: Akzo Nobel N.V., Arnhem, Netherlands

[21] Appl. No.: 477,839

[22] Filed: Jun. 7, 1995

Related U.S. Application Data

[63] Continuation-in-part of Ser. No. 389,986, Feb. 14, 1995.
[51] Int. Cl.$^6$ .......................... G01N 33/49; G06F 19/00
[52] U.S. Cl. ..................... 364/497; 364/413.08; 436/66
[58] Field of Search .................. 364/413.01, 413.02, 364/413.07, 413.08, 413.09, 497, 498, 496; 395/924; 356/39; 382/133, 134; 436/66

[56] References Cited

U.S. PATENT DOCUMENTS

| | | | |
|---|---|---|---|
| 4,199,748 | 4/1980 | Bacus | 364/413.08 |
| 4,998,535 | 3/1991 | Selker et al. | 128/696 |
| 5,156,974 | 10/1992 | Grossman et al. | 364/413.09 |
| 5,388,164 | 2/1995 | Yonekawa et al. | 382/134 |
| 5,473,732 | 12/1995 | Chang | 395/77 |

OTHER PUBLICATIONS

J. Sweeney et al., *Journal of the American Society of Hematology*, 76:10(1) Poster #1745, Nov. 15, 1990.
J. Sweeney et al., *Journal of the American Society of Hematology*, 74:7(1) Poster #1509, Nov. 1989.
J.W. Furlong et al., *Am. J. Clin. Pathol.*, 96:1:134–141, Jul. 1991.
J. Boone et al., *Neural Networks in Radiologic Diagnosis*, 25:9:1013–1023 (Sep. 1990).
M.A. Khanin et al., *J. Theor. Biol.*, 136:127–134 (1989).
P. Baumann et al., *Haemostasis*, 19:309–321 (1989).
C.C. Heuck et al., *Haemostasis*, 21:10–18 (1991).
J.F. Hoffman et al., "The Coag-A-Mate RA4 Fibrinogen Assay" Organon Teknika (1990).
B. Pohl et al., *Haemostasis*, 24:325–337 (1994).
A.L. Astion et al., *Arch Pathol Lab Med*, 116:995–1001 (1992).
W.R.M. Dassen et al., *Journal of Electrocardiology*, 23 (Supp.) 201–202.
J.A. Swets et al., *Science*, 240:1285–1293 (Jun. 3, 1988).
D.A. Bluestein et al., *Nurse Practitioner5*, 17:7:39–45 (Jul. 1991).
J.T. Brandt et al., *Arch Pathol Lab Med*, 115:109–114 (1991).
I. Talstad, *Haemostasis*, 23:19–25, 1993.
E. Baum et al., *MIT Press*, 81–89, 1989.
M.L. Asiton et al., *Clin. Chem.*, 39/9 1998–2004, (1993).
M.H. Zweig et al., *Clin. Chem.*, 39/4 561–577 (1993).
C.R. Schweiger et al. *Clin. Chem.*, 39/9 1966–1971 (1993).

*Primary Examiner*—Edward R. Cosimano
*Assistant Examiner*—Kyle J. Choi
*Attorney, Agent, or Firm*—Gregory R. Muir

[57] ABSTRACT

A method and apparatus are disclosed for predicting the presence of at least one congenital or acquired imbalance or therapeutic condition associated with thrombosis/hemostasis from at least one time-dependent measurement profile. At least one time-dependent measurement on an unknown sample is performed and a respective property of said sample is measured over time so as to derive a time-dependent measurement profile. A set of a plurality of predictor variables are defined which sufficiently define the data of the time-dependent measurement profile. A model is then derived that represents the relationship between the congenital or acquired imbalance or therapeutic condition, and the set of predictor variables. Subsequently, the model is utilized to predict the existence of the congenital or acquired imbalance or therapeutic condition in the unknown sample.

38 Claims, 14 Drawing Sheets

| Hidden Layer Size | Error | | $\varphi_{ODB}$ |
|---|---|---|---|
| | $E_{tr}$ | $E_{cv}$ | |
| 2 | 0.384 | 0.376 | 0.848 |
| 4 | 0.386 | 0.354 | 0.835 |
| 6 | 0.341 | 0.328 | 0.875 |
| 8 | 0.358 | 0.327 | 0.857 |
| 10 | 0.346 | 0.325 | 0.856 |
| 12 | 0.347 | 0.322 | 0.855 |

FIG. 9

| Predictor Variable | Description |
|---|---|
| $pv_{f1} = \left(\dfrac{dT}{dt}\right)_{min}$ | minimum of the first derivative |
| $pv_{f2} = t \text{ at } \left(\dfrac{dT}{dt}\right)_{min}$ | time index of the minimum of the first derivative |
| $pv_{f3} = \left(\dfrac{d_2T}{dt^2}\right)_{min}$ | minimum of the second derivative |
| $pv_{f4} = t \text{ at } \left(\dfrac{dT^2}{dt^2}\right)_{min}$ | index of the minimum of the second derivative |
| $pv_{f5} = \left(\dfrac{d^2T}{dt^2}\right)_{max}$ | maximum of the second derivative |
| $pv_{f6} = t \text{ at } \left(\dfrac{dT^2}{dt^2}\right)_{max}$ | index of the maximum of the second derivative |
| $pv_{f7} = T_{f_0} - T_{f_n}$ | overall change in transmittence during the reaction |

FIG. 13

METHOD AND APPARATUS FOR PREDICTING THE PRESENCE OF CONGENITAL AND ACQUIRED IMBALANCES AND THERAPEUTIC CONDITIONS

BACKGROUND OF THE INVENTION

This application is a continuation-in-part of U.S. patent application Ser. No. 08/389,986 to Fischer et al. filed Feb. 14, 1995, the subject matter of which is incorporated herein by reference. This application is also related to the following publications, the subject matter of each also being incorporated herein by reference:

1. B. Pohl, C. Beringer, M. Bombard, F. Keller, The quick machine—a mathematical model for the extrinsic activation of coagulation, *Haemostasis*, 24, 325–337 (1994).

2. J. Brandt, D. Triplett, W. Rock, E. Bovill, C. Arkin, Effect of lupus anticoagulants on the activated partial thromboplastin time, *Arch Pathol Lab Med*, 115, 109–14 (1991).

3. I. Talstad, Which coagulation factors interfere with the one-stage prothrombin time?, *Haemostasis*, 23, 19–25 (1993).

4. P. Baumann, T. Jurgensen, C. Heuck, Computerized analysis of the in vitro activation of the plasmatic clotting system, *Haemostasis*, 19, 309–321 (1989).

5. C. Heuck, P. Baumann, Kinetic analysis of the clotting system in the presence of heparin and depolymerized heparin, *Haemostasis*, 21, 10–18 (1991).

6. M. Astion and P. Wilding, The application of back-propagation neural networks to problems in pathology and laboratory medicine, *Arch Pathol Lab Med*, 116, 995–1001 (1992).

7. M. Astion, M. Wener, R. Thomas, G. Hunder, and D. Bloch, Overtraining in neural networks that interpret clinical data, *Clinical Chemistry*, 39, 1998–2004 (1993).

8. J. Furlong, M. Dupuy, and J. Heinsimer, Neural network analysis of serial cardiac enzyme data, *A.J.C.P.*, 96, 134–141 (1991).

9. W. Dassen, R. Mulleneers, J. Smeets, K. den Dulk, F. Cruz, P. Brugada, and H. Wellens, Self-learning neural networks in electrocardiography, *J. Electrocardiol*, 23, 200–202 (1990).

10. E. Baum and D. Haussler, What size net gives valid generalization? *Advances in Neural Information Processing Systems*, Morgan Kauffman Publishers, San Mateo, Calif., 81–90 (1989).

11. A. Blum, Neural Networks in C++, John Wiley & Sons, New York, (1992).

12. S. Haykin, *Neural Networks A Comprehensive Foundation*, Macmillan College Publishing Company, New York, (1994).

13. J. Swets, Measuring the accuracy of diagnostic systems, *Science*, 240, 1285–1293 (1988).

14. M. Zweig and G. Campbell, Receiver-operating characteristic (ROC) plots: a fundamental evaluation tool in clinical medicine, *Clinical Chemistry*, 39, 561–577 (1993).

15. D. Bluestein, L. Archer, The sensitivity, specificity and predictive value of diagnostic information: a guide for clinicians, *Nurse Practitioner*, 16, 39–45 (1991).

16. C. Schweiger, G. Soeregi, S. Spitzauer, G. Maenner, and A. Pohl, Evaluation of laboratory data by conventional statistics and by three types of neural networks, *Clinical Chemistry*, 39, 1966–1971 (1993).

Blood clots are the end product of a complex chain reaction where proteins form an enzyme cascade acting as a biologic amplification system. This system enables relatively few molecules of initiator products to induce sequential activation of a series of inactive proteins, known as factors, culminating in the production of the fibrin clot. Mathematical models of the kinetics of the cascade's pathways have been previously proposed.

In [1], a dynamic model of the extrinsic coagulation cascade was described where data were collected for 20 samples using quick percent, activated partial thromboplastin time (APTT), thrombin time (TT), fibrinogen, factor(F) II, FV, FVII, FX, antithrombin III (ATIII), and factor degradation product (FDP) assays. These data were used as input to the model and the predictive output compared to actual recovered prothrombin time (PT) screening assay results. The model accurately predicted the PT result in only 11 of 20 cases. These coagulation cascade models demonstrate: (1) the complexity of the clot formation process, and (2) the difficulty in associating PT clot times alone with specific conditions.

Thrombosis and hemostasis testing is the in vitro study of the ability of blood to form clots and to break clots in vivo. Coagulation (hemostasis) assays began as manual methods where clot formation was observed in a test tube either by tilting the tube or removing fibrin strands by a wire loop. The goal was to determine if a patient's blood sample would clot after certain materials were added. It was later determined that the amount of time from initiation of the reaction to the point of clot formation in vitro is related to congenital disorders, acquired disorders, and therapeutic monitoring. In order to remove the inherent variability associated with the subjective endpoint determinations of manual techniques, instrumentation has been developed to measure clot time, based on (1) electromechanical properties, (2) clot elasticity, (3) light scattering, (4) fibrin adhesion, and (5) impedance. For light scattering methods, data is gathered that represents the transmission of light through the specimen as a function of time (an optical time-dependent measurement profile).

Two assays, the PT and APTT, are widely used to screen for abnormalities in the coagulation system, although several other screening assays can be used, e.g. protein C, fibrinogen, protein S and/or thrombin time. If screening assays show an abnormal result, one or several additional tests are needed to isolate the exact source of the abnormality. The PT and APTT assays rely primarily upon measurement of time required for clot time, although some variations of the PT also use the amplitude of the change in optical signal in estimating fibrinogen concentration.

Blood coagulation is affected by administration of drugs, in addition to the vast array of internal factors and proteins that normally influence clot formation. For example, heparin is a widely-used therapeutic drug that is used to prevent thrombosis following surgery or under other conditions, or is used to combat existing thrombosis. The administration of heparin is typically monitored using the APTT assay, which gives a prolonged clot time in the presence of heparin. Clot times for PT assays are affected to a much smaller degree. Since a number of other plasma abnormalities may also cause prolonged APTT results, the ability to discriminate between these effectors from screening assay results may be clinically significant.

Using a sigmoidal curve fit to a profile, Baumann, et al [4] showed that a ratio of two coefficients was unique for a select group of blood factor deficiencies when fibrinogen was artificially maintained by addition of exogenous fibrinogen to a fixed concentration, and that same ratio also correlates heparin to FII deficiency and FXa deficiencies.

However, the requirement for artificially fixed fibrinogen makes this approach inappropriate for analysis of clinical specimens. The present invention makes it possible to predict a congenital or acquired imbalance or therapeutic condition for clinical samples from a time-dependent measurement profile without artificial manipulation of samples.

The present invention was conceived of and developed for predicting the presence of congenital or acquired imbalances or therapeutic conditions of an unknown sample based on one or more time-dependent measurement profiles, such as optical time-dependent measurement profiles, where a set of predictor variables are provided which define characteristics of profile, and where in turn a model is derived that represents the relationship between a congenital or acquired imbalance or therapeutic condition and the set of predictor variables (so as to, in turn, utilize this model to predict the existence of the congenital or acquired imbalance or therapeutic condition in the unknown sample).

SUMMARY OF THE INVENTION

The present invention is directed to a method and apparatus for predicting the presence of at least one congenital or acquired imbalance or therapeutic condition from at least one time-dependent measurement profile. The method and apparatus include a) performing at least one assay on an unknown sample and measuring a respective property over time so as to derive a time-dependent measurement profile, b) defining a set of predictor variables which sufficiently define the data of the time-dependent profile, c) deriving a model that represents the relationship between a diagnostic output and the set of predictor variables, and d) utilizing the model to predict the existence of a congenital or acquired imbalance or therapeutic condition in the unknown sample relative to the diagnostic output. In one embodiment, training data is provided by performing a plurality of assays on known samples, the model is a multilayer perceptron, the relationship between the diagnostic output and the set of predictor variables is determined by at least one algorithm, and the at least one algorithm is a back propagation learning algorithm. In a second embodiment of the present invention, the relationship between the diagnostic output and the set of predictor variables is derived by a set of statistical equations.

Also in the present invention, a plurality of time-dependent measurement profiles are derived, which time-dependent measurement profiles can be optical time-dependent measurement profiles such as ones provided by a automated analyzer for thrombosis and hemostasis, where a plurality of optical measurements are taken over time, and where the plurality of optical measurements are normalized. The optical profiles can include one or more of a PT profile, a fibrinogen profile, an APTT profile, a TT profile, a protein C profile, a protein S profile and a plurality of other assays associated with congenital or acquired imbalances or therapeutic conditions.

BRIEF DESCRIPTION OF THE DRAWINGS

FIG. 9 is a Table comparing hidden layer size with prediction error;

FIG. 13 is a chart listing examples of predictor variables for use in the present invention.

DESCRIPTION OF THE PREFERRED EMBODIMENTS

Figure 14:
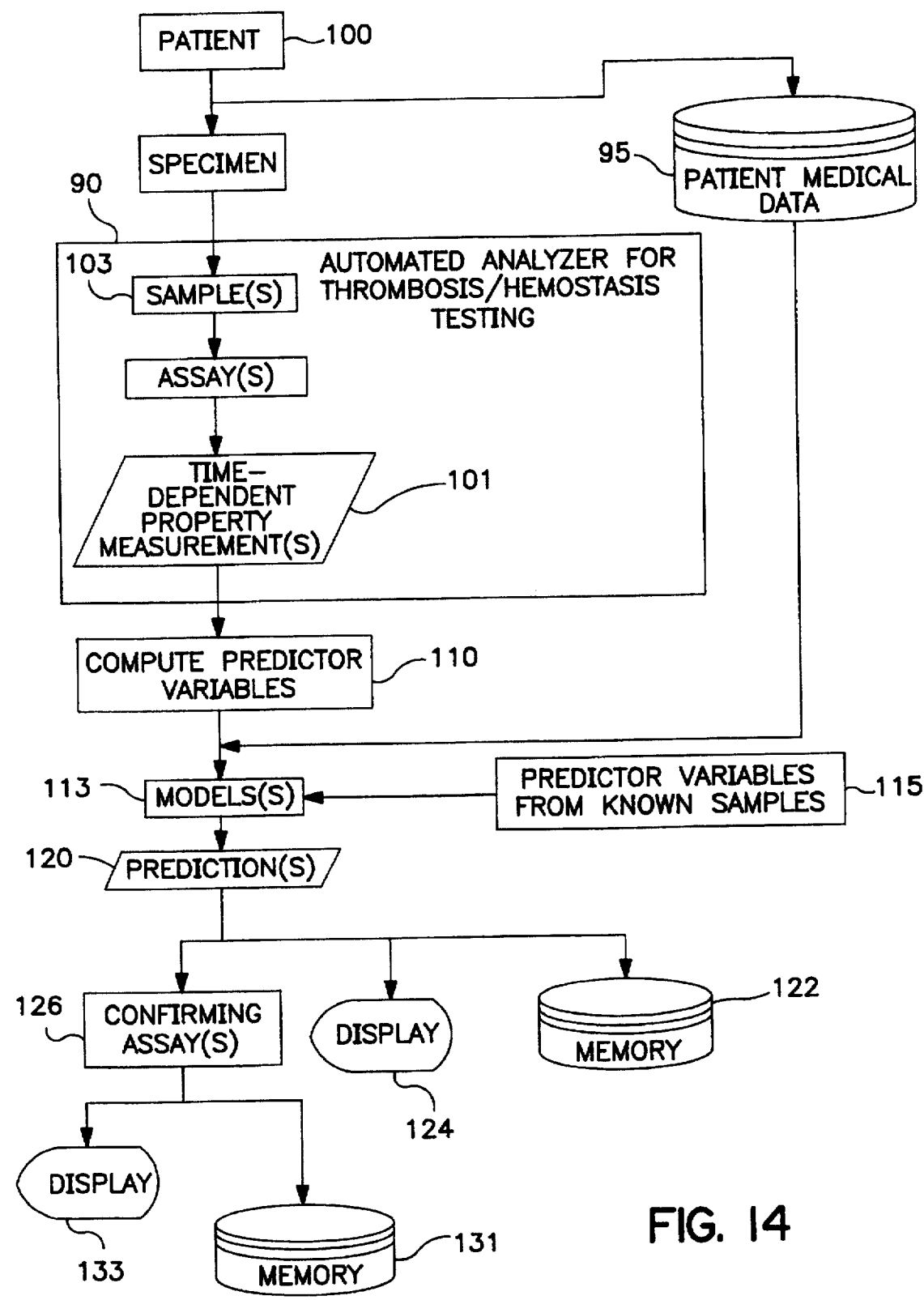
FIG. 14 is a chart illustrating key aspects of the present invention.

In the present invention, both a method and apparatus are provided for predicting the presence of at least one congenital or Acquired imbalance or therapeutic condition. As can be seen in FIG. 14, one or more time-dependent measurements (101) are performed on an unknown sample (103). The term "time-dependent measurement" is referred to herein to include measurements derived from assays (e.g. PT, APTT, fibrinogen, protein C, protein S, TT, ATIII, plasminogen and factor assays). The terms "unknown sample" and "clinical sample" refer to a sample, such as one from a medical patient (100), where a congenital or acquired imbalance or therapeutic condition associated with thrombosis/hemostasis is not known (or, if suspected, has not been confirmed). In the present invention, a coagulation property is measured over time so as to derive a time-dependent measurement profile. In a preferred embodiment, the time-dependent measurement is an optical measurement for deriving an optical profile. For example, a PT profile, a fibrinogen profile, a TT profile, an APTT profile and/or variations thereof can be provided where, an unknown sample is analyzed for clot formation based on light transmittance over time through the unknown sample. In another preferred embodiment, two (or more) optical profiles are provided, such as both a PT profile and an APTT profile.

After the time-dependent measurement profiles are provided, a set of predictor variables are defined (110) which sufficiently define the data of the time-dependent profile. One or more predictor variables comprise the set. And, in one embodiment, three or more, and in a preferred embodiment, four or more predictor variables were found to desirably make up the set. It was found that the characteristics of the time-dependent measurement profile could best be defined by one or more predictor variables, including the minimum of the first derivative of the optical profile, the time index of this minimum, the minimum of the second derivative of the optical profile, the time index of this minimum, the maximum of the second derivative, the time index of this maximum, the overall change in transmittance during the time-dependent measurement, clotting time, slope of the optical profile prior to clot formation, and slope of the optical profile after clot formation.

After defining the set of predictor variables, a model is derived which represents the relationship between a congenital or acquired imbalance or therapeutic condition and the set of predictor variables. This model can be derived from a neural network in one embodiment of the present invention. In another embodiment, the model is derived via a set of statistical equations.

Neural networks represent a branch of artificial intelligence that can be used to learn and model complex, unknown systems given some known data (115) from which it can train. Among the features of neural networks that make them an attractive alternative for modeling complex systems are:
1. They can handle noisy data well and recognize patterns even when some of the input data are obscured or missing.
2. It is unnecessary to determine what factors are relevant a priori since the network will determine during the training phase what data are relevant, assuming there are at least some meaningful parameters in the set.

Figure 1:
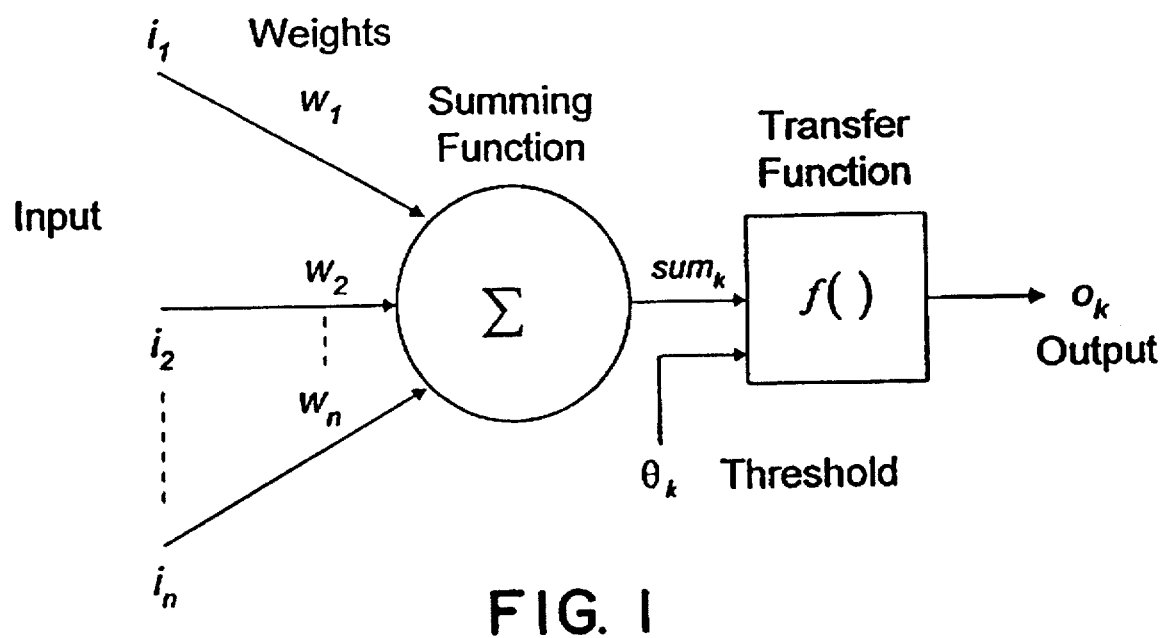
FIG. 1 is a general neuron diagram relating to the embodiment of the present invention utilizing a neural network.

Neural networks are formed from multiple layers of interconnected neurons like that shown in FIG. 1. Each neuron has one output and receives input $i_1 \ldots i_n$ from multiple other neurons over connecting links, or synapses. Each synapse is associated with a synaptic weight, $w_j$. An adder $\Sigma$ or linear combiner sums the products of the input signals and synaptic weights $i_j * w_j$. The linear combiner output $sum_1$ and $\theta_1$ (a threshold which lowers or a bias which raises the output) are the input to the activation function $f()$. The synaptic weights are learned by adjusting their values through a learning algorithm.

After deriving the model (113), whether based on neural networks or statistical equations, the model is utilized to predict (120) the existence of a congenital or acquired imbalance or therapeutic condition in the unknown sample relative to the time-dependent measurement profile(s). As such, a congenital or acquired imbalance or therapeutic condition can be predicted. Conditions which can be predicted as being abnormal in the present invention can include, among others, a) factor deficiencies, e.g. fibrinogen, Factors II, V, VII, VIII, IX, X, XI and XII, as well as ATIII, plasminogen, protein C, protein S, etc., b) therapeutic conditions, e.g. heparin, coumadin, etc., and c) conditions such as lupus anticoagulant. In one embodiment of the present invention, the method is performed on an automated analyzer (90). The time-dependent measurement profile, such as an optical data profile, can be provided automatically by the automated analyzer, where the unknown sample is automatically removed by an automated probe from a sample container to a test well, one or more reagents are automatically added to the test well so as to initiate the reaction within the sample. A property over time is automatically optically monitored so as to derive the optical profile. The predicted congenital or therapeutic condition (120) can be automatically stored in a memory (122) of an automated analyzer and/or displayed (124) on the automated analyzer, such as on a computer monitor, or printed out on paper. As a further feature of the invention, if the predicted congenital or acquired imbalance or therapeutic condition is an abnormal condition, then one or more assays for confirming the existence of the abnormal condition (126) are performed on the automated analyzer. In fact, in a preferred embodiment, the one or more confirming assays are automatically ordered and performed on the analyzer once the predicted condition is determined, with the results of the one or more confirming assays being stored in a memory (131) of the automated analyzer and/or displayed (133) on the analyzer. Also, where the unknown sample is from a medical patient, both the derived model and other patient medical data (95) can be used for predicting the imbalance/condition.

EXAMPLE 1

Prediction of Heparin in Sample

This example shows a set of predictor variables that adequately describe screening assay optical profiles, develops an optimal neural network design, and determines the predictive capabilities of an abnormal condition associated with thrombosis/hemostasis (in this case for the detection of heparin) with a substantial and well-quantified test data set.

Simplastin™ L, Platelin™ L, calcium chloride solution (0.025M), imidazole buffer were obtained from Organon Teknika Corporation, Durham, N.C., 27712, USA. All plasma specimens were collected in 3.2% or 3.8% sodium citrate in the ratio of one part anticoagulant to nine parts whole blood. The tubes were centrifuged at 2000 g for 30 minutes and then decanted into polypropylene tubes and stored at −80° C. until evaluated. 757 specimens were prepared from 200 samples. These specimens were tested by the following specific assays: FII, FV, FVII, FVIII, FIX, FX, FXI, FXII, heparin, fibrinogen, plasminogen, protein C, and AT-III. Samples represented normal patients, a variety of deficiencies, and therapeutic conditions. Of the specimen population 216 were positive for heparin determined by a heparin concentration greater than 0.05 units/ml measured with a chromogenic assay specific for heparin. The remaining specimens, classified as heparin-negative, included normal specimens, a variety of single or multiple factor deficiencies, and patients receiving other therapeutic drugs. Positive heparin samples ranged to 0.54 units/ml.

PT and APTT screening assays were performed on each specimen utilizing two automated analyzers (MDA™ 180s) and multiple reagent and plasma vials (Organon Teknika Corporation, Durham N.C. 27712, USA) over a period of five days. When clot-based coagulation assays are performed by an automated optically-based analyzer such as the MDA 180, data are collected over time that represents the normalized level of light transmission through a sample as a clot forms (the optical profile). As the fibrin clot forms, the transmission of light is decreased. The optical profile was stored from each test.

Figure 2:
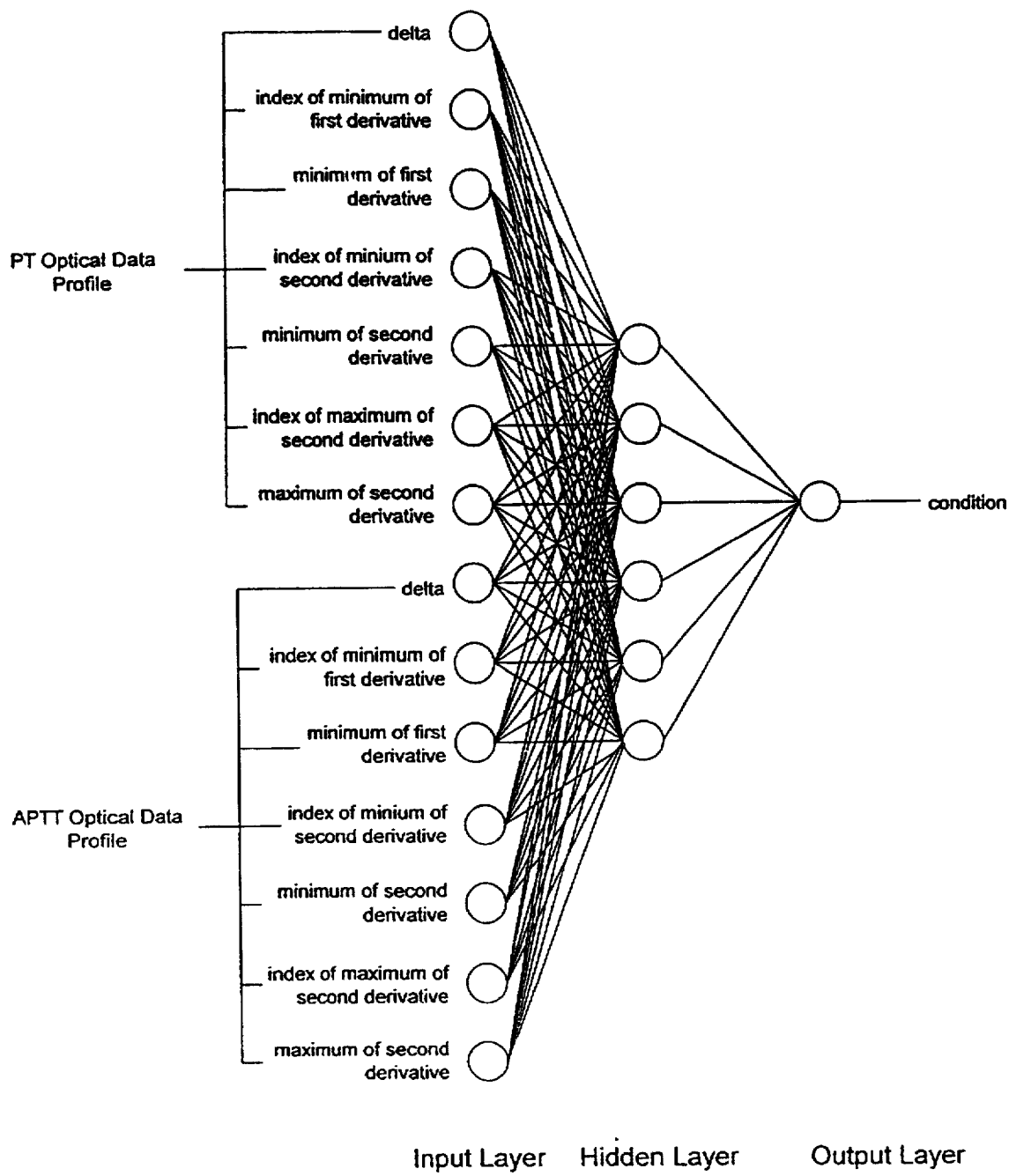
FIG. 2 is a diagram of a multilayer perceptron for predicting congenital or acquired imbalances or therapeutic conditions, relating to the neural network embodiment of the present invention.

The network configuration chosen, a multilayer perceptron (MLP) maps input predictor variables from the PT and APTT screening assays to one output variable (see FIG. 2) which represents a single specified condition. A similar network was also employed for PT-only variables and APTT-only variables. This specific MLP consists of three layers: the input layer, one hidden layer, and the output layer.

Figure 3:
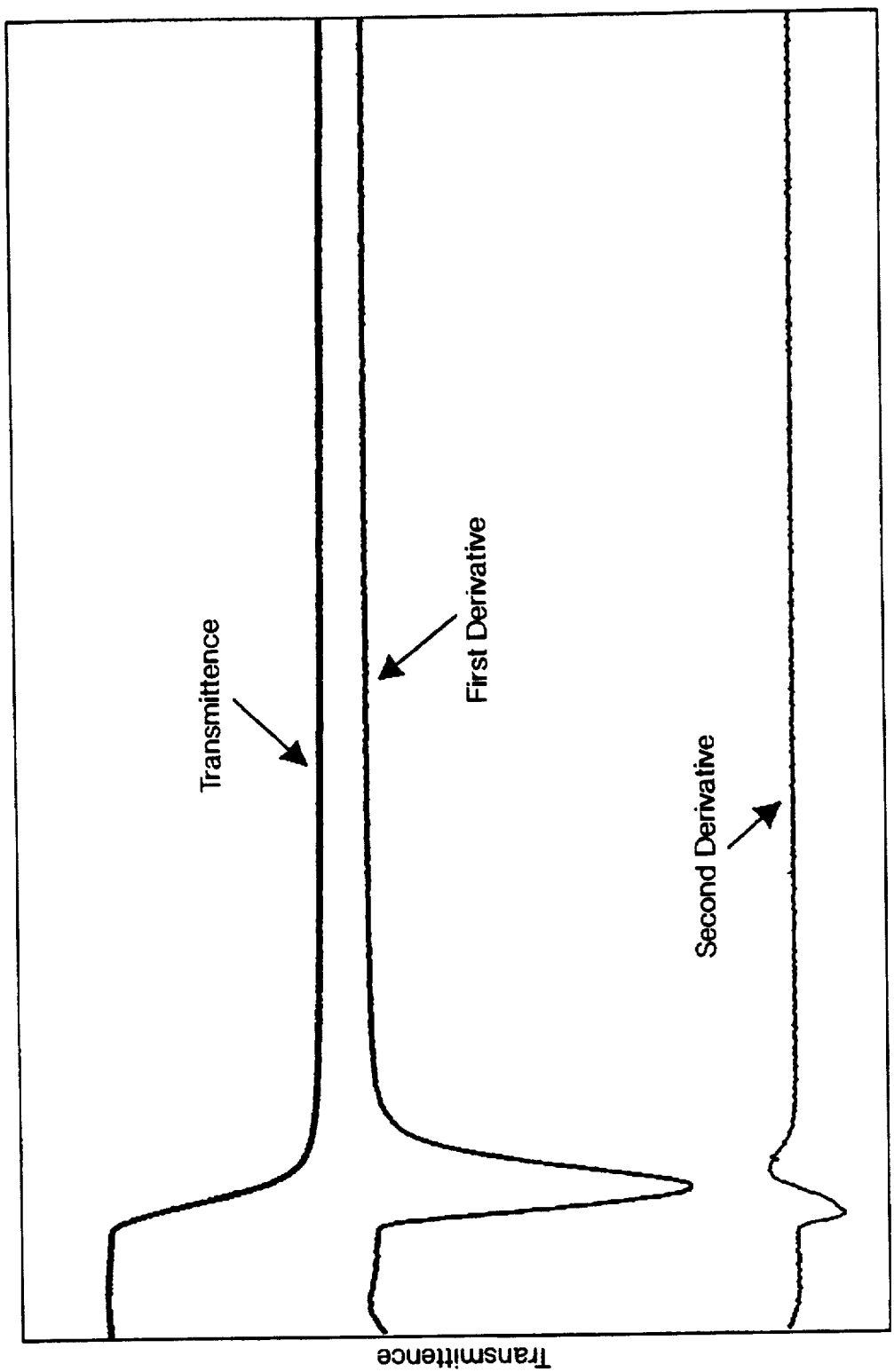
FIG. 3 is an optical profile with first and second derivatives of a normal clotting sample.

A normal optical profile is shown in FIG. 3. The set of predictor variables were chosen with the intent of describing optical profiles as completely as possible with a minimum number of variables. They are summarized in Table 1 where t is time from initiation of reaction, T is normalized light transmission through the reaction mixture, and $pv_{j,k}$ is the kth predictor variable of assay j.

The predictor variables were scaled to values between 0 and 1, based on the range of values observed for each variable for assay type k $$i_j = f(pv_{j,k}, (pv_{j,n,k})_{min}, (pv_{j,n,k})_{max}).$$

The input variable set includes $i_1 \ldots_7$ for both a PT assay and APTT assay for each specimen. For known output variable values, heparin samples with results of greater than 0.05 units/ml were considered positive and assigned a value of 1 while negative samples were assigned a value of 0.

As the ratio of training set sample to the number of weights in a network decreases, the probability of generalizing decreases, reducing the confidence that the network will lead to correct classification of future samples taken from the same distribution as the training set. Thus, small samples sizes, then can lead to artificially high classification rates. This phenomenon is known as overtraining. In order to achieve a true accuracy rate of 80%, a guideline for the number of samples in the training set is approximately five times the number of weights in the network. For most of this work, a 14-6-1 network was used, leading to an upward bound on the sample size of O(450). To monitor and evaluate the performance of the network and its ability to generalize, a cross-validation set is processed at the end of each training epoch. This cross-validation set is a randomly determined subset of the known test set that is excluded from the training set.

Once the input predictor variables and output values were determined for all specimen optical profiles, the 757 sets of data were randomly distributed into two groups: 387 were used in the training set and 370 were used in the cross-validation set. These same two randomly determined sets were used throughout all the experiments.

All synaptic weights and threshold values were initialized at the beginning of each training session to small random numbers.

The error-correction learning rule is an iterative process used to update the synaptic weights by a method of gradient descent in which the network minimizes the error as pattern associations (known input-output pairs) in the training set are presented to the network. Each cycle through the training set is known as an epoch. The order or presentation of the pattern associations was the same for all epochs. The learning algorithm consists of six steps which make up the forward pass and the backward pass. In the forward pass, the hidden layer neuron activations are first determined $$h=F(iW1+\theta_h)$$

where h is the vector of hidden-layer neurons, i the vector of input-layer neurons, W1 the weight matrix between the input and hidden layers, and F() the activation function. A logistic function is used as the activation function $$F(x) = \frac{1}{1+e^{-x}} .$$

Then the output-layer neurons are computed $$o=F(hW2+\theta_o)$$

where o represents the output layer, h the hidden layer and W2 the matrix of synapses connecting the hidden layer and output layers. The backward pass begins with the computation of the output-layer error $$e_0=(o-d),$$

where d is the desired output. If each element of $e_o$ is less than some predefined training error tolerance vector $TE_{tol}$, than the weights are not updated during that pass and the process continues with the next pattern association. A training error tolerance of 0.1 was used in all experiments unless otherwise specified. Otherwise, the local gradient at the output layer is then computed:

$$g_o=o(1-o)e_0.$$

Next, the hidden-layer local gradient is computed:

$$g_h=h(1-h)W2g_o.$$

Once the hidden layer error is calculated, the second layer of weights is adjusted $$W2_m=W2_{m-1}+\Delta W2$$

where $$\Delta W2=\eta hg_o+\gamma\Delta W2_{m-1}.$$

is the learning rate, γ is the momentum factor, and m is the learning iteration. The first layer of weights is adjusted in a similar manner $$W1_m=W1_{m-1}+\Delta W1$$

where $$\Delta W1=\eta ie+\gamma\Delta W1_{m-1}.$$

The forward pass and backward pass are repeated for all of the pattern associations in the training set, referred to as an epoch, 1000 times. At the end of each epoch, the trained network is applied to the cross-validation set.

Several methods were employed to measure the performance of the network's training. Error, E, for each input set was defined as $$E=\sqrt{\frac{1}{N}\sum_{q=1}^{N}(d_q-o_q)^2} .$$

The learning curve is defined as the plot of E versus epoch. The percent classification, φ, describes the percent of the total test set (training and cross-validation) that is correctly classified based on some defined decision boundary, β. Receiver-Operating Characteristic (ROC) plots have also been utilized to describe trained networks' ability to discriminate between the alternative possible outcome states. In these plots, measures of sensitivity and specificity are shown for a complete range of decision boundaries. The sensitivity, or true-positive fraction is defined as $$\text{sensitivity} = \frac{\text{true positive}}{\text{true positive + false negative}}$$

and the false-positive fraction, or (1-specificity) is defined as $$(1-\text{specificity}) = \frac{\text{false positive}}{\text{false positive + true negative}} .$$

These ROC plots represent a common tool for evaluating clinical laboratory test performance.

Using the test set described, experiments were performed to determine if the presence of heparin could be predicted with this method. First, experiments were conducted to determine optimal error-correction backpropagation learning parameters: (1) hidden layer size, (2) learning rate, and (3) momentum. Additional experiments were also conducted to compare the performance of networks based on PT and APTT assays alone with that of one combining the results of both, the effect of the training error tolerance, and the decision boundary selection.

FIG. 9 shows the effect of the hidden layer size on the training and cross validation error and the percent correct classification for the optimal decision boundary, defined as the decision boundary which yielded the lowest total number of false positives and false negatives from the total test set. As the hidden layer size is increased, the error is decreased. However, the ability to generalize does not increase after a hidden layer size of 6. The most significant benefit in terms of both error and percentage correct classification is between 4 and 6. A hidden layer size of 6 was used for the remainder of the experiments.

Figure 4:
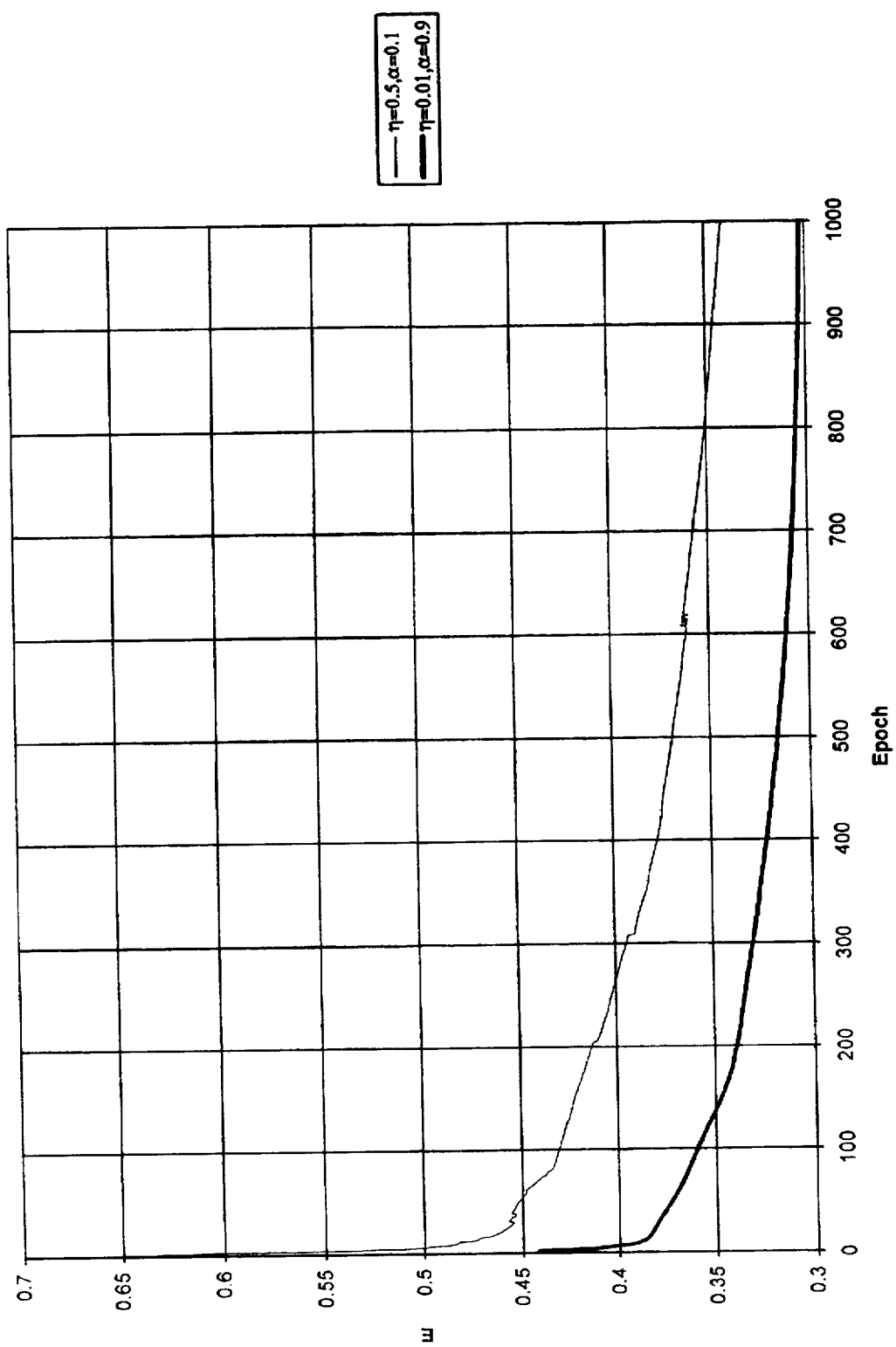
FIG. 4 is an illustration of two learning curves.
Figure 5:
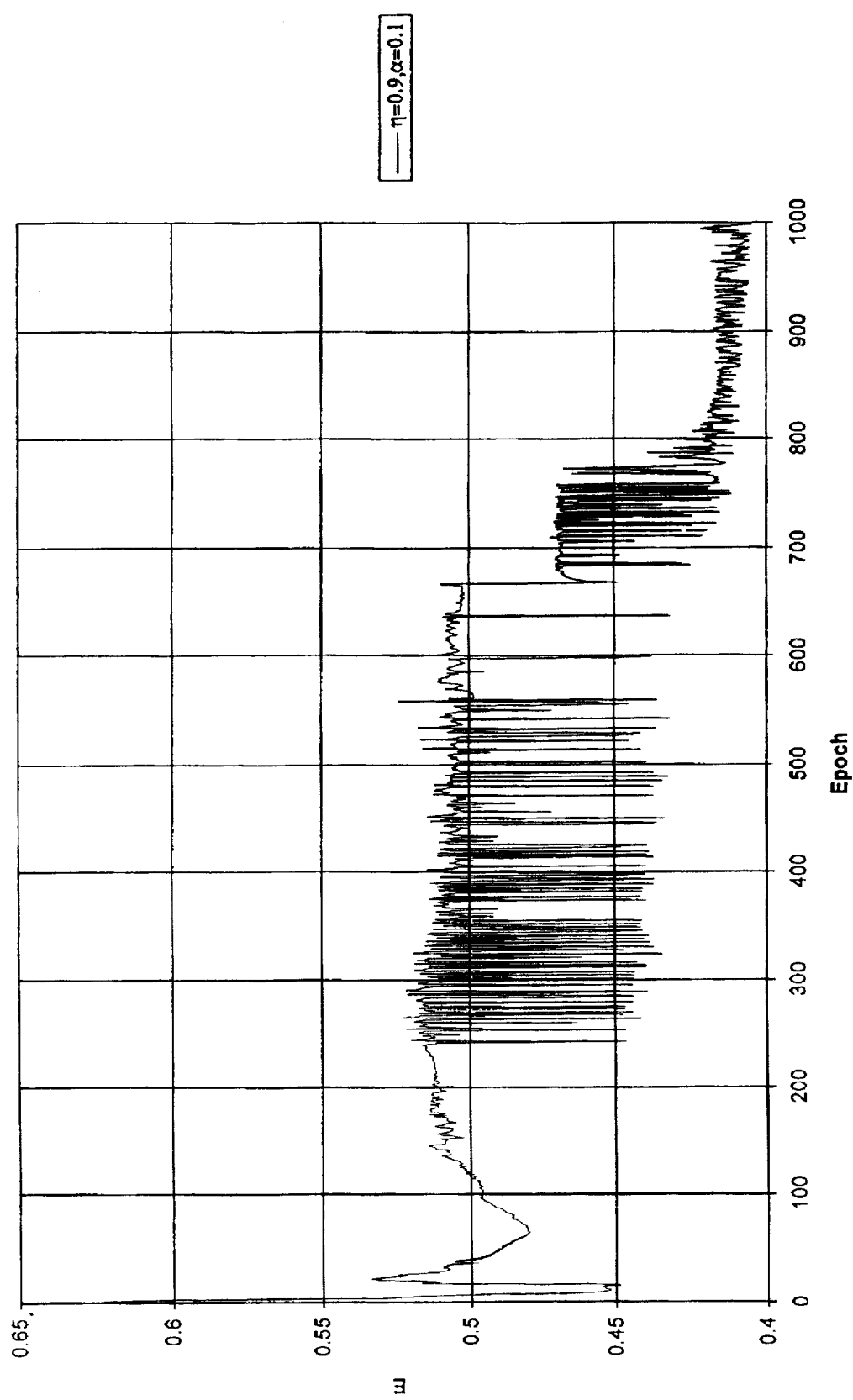
FIG. 5 is an illustration of an unstable learning curve.

A series of experiments were conducted with $\eta=\{0.01, 0.1, 0.5, 0.9\}$ and $\gamma=\{0.0, 0.1, 0.5, 0.9\}$. FIG. 4 shows the learning curves for two of the best combinations of parameters. FIG. 5 shows an example learning curve when the learning rate is so high it leads to oscillations and convergence to a higher E. In general, as $\eta \rightarrow 0$ the network converged to a lower E and as $\gamma \rightarrow 1$, the rate of convergence improved. As $\eta \rightarrow 1$, the value of E converged too increased and oscillations increased. In addition, as $\eta \rightarrow 1$, $\gamma \rightarrow 1$ exacerbated the oscillations.

Figure 6:
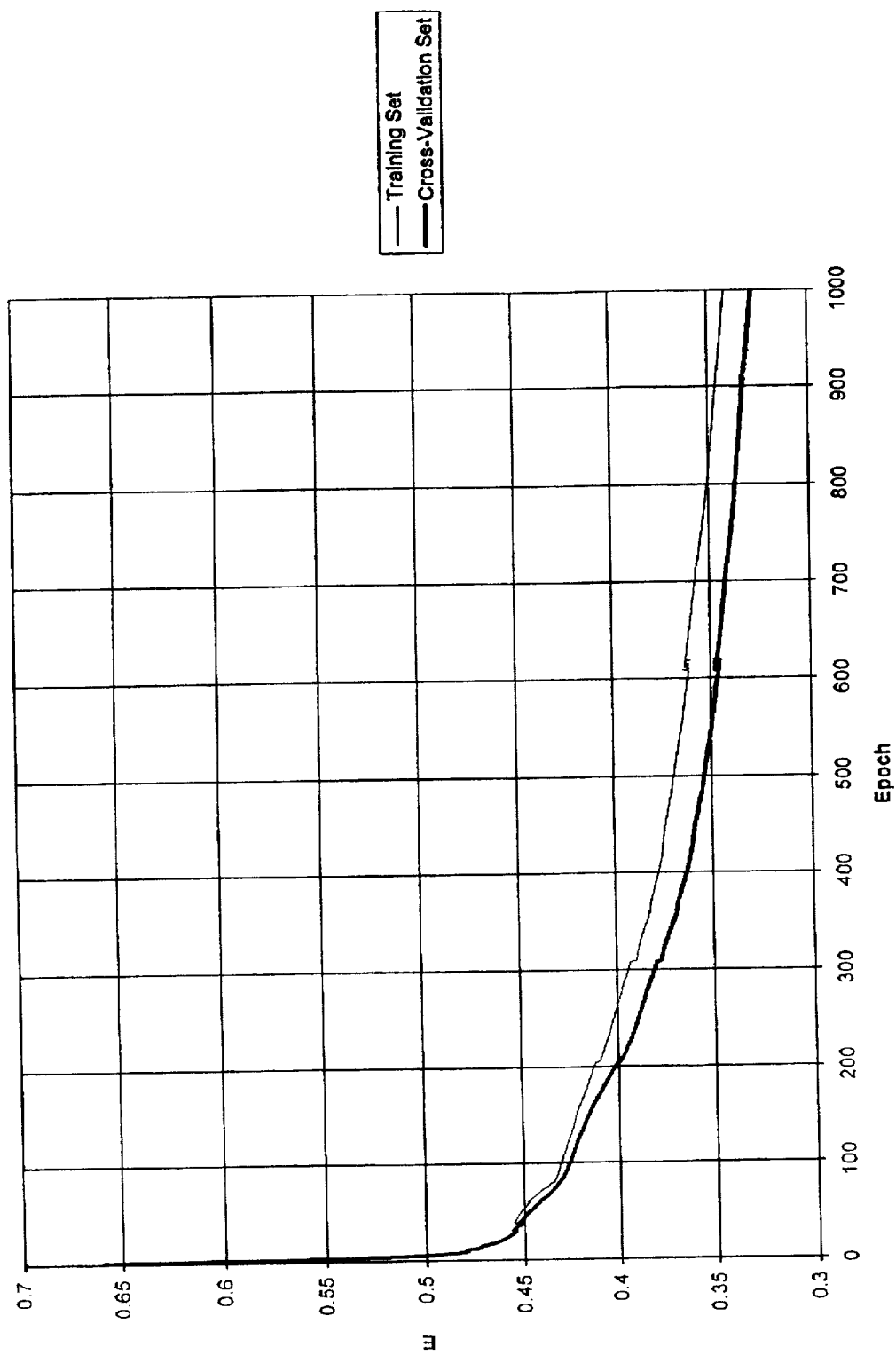
FIG. 6 is a graph showing a comparison of training and cross-validation learning curves.

FIG. 6 shows a comparison of the learning curve for the training set and cross-validation set for $\eta=0.5$ and $\gamma=0.1$. It is a primary concern when developing neural networks, and it has been previously shown that it is important to look not only at the error in the training set for each cycle, but also the cross-validation error.

Figure 7:
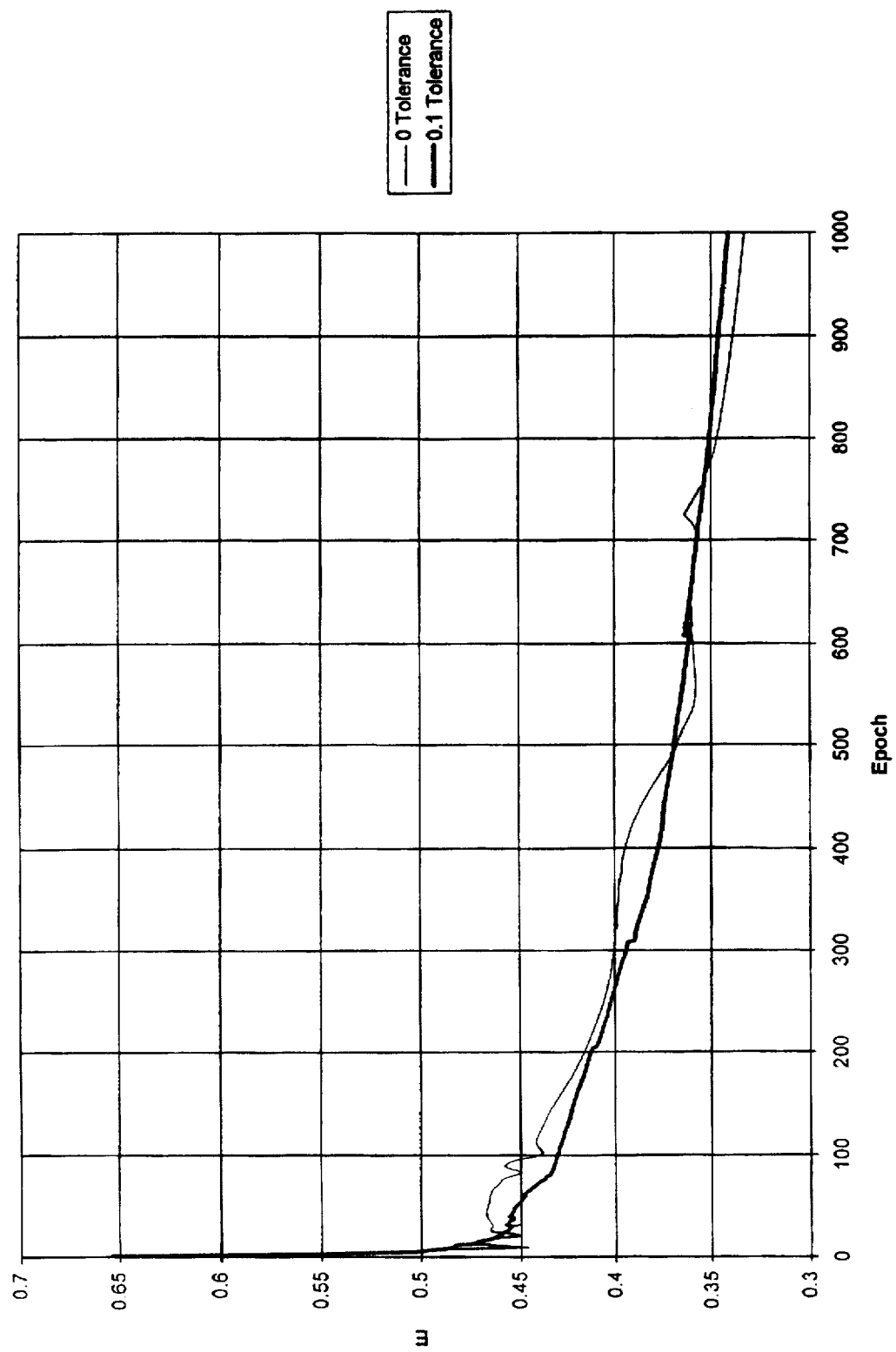
FIG. 7 is a graph showing a comparison of training error for training tolerances of 0.0 and 0.1.

FIG. 7 shows the learning curve $\eta=0.5$ and $\gamma=0.1$ and a learning tolerance of 0.0 and 0.1. These results suggest that a small learning tends to smoothen the convergence of the learning process.

Figure 8:
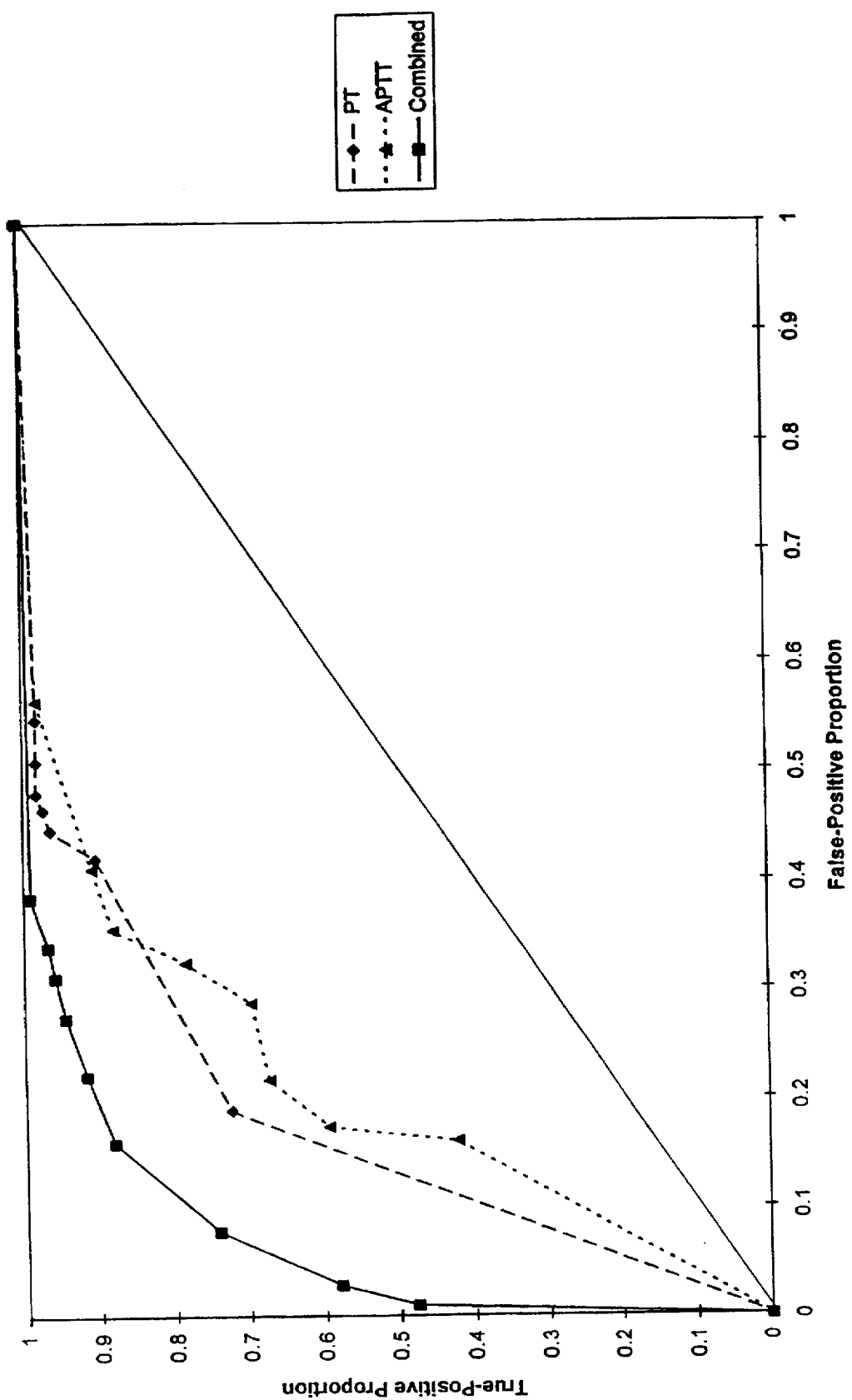
FIG. 8 is a ROC illustrating the effect of decision boundary on classification.

FIG. 8 shows the ROC plot for networks trained with the predictor variables from each of the two screening assays with that of them combined. In the single assay cases, the hidden layer size was 3. While using the data from one assay does lead to some success, using the information from both assays makes a significant improvement in the ability of the network to correctly predict the presence of heparin. This graph indicates that a 90% true positive proportion can be achieved with a false positive proportion of 15%. Using a single assay, a 60-70% true positive proportion can be achieved with a false positive proportion of approximately 15%.

EXAMPLE 2

Factor VIII

Figure 10:
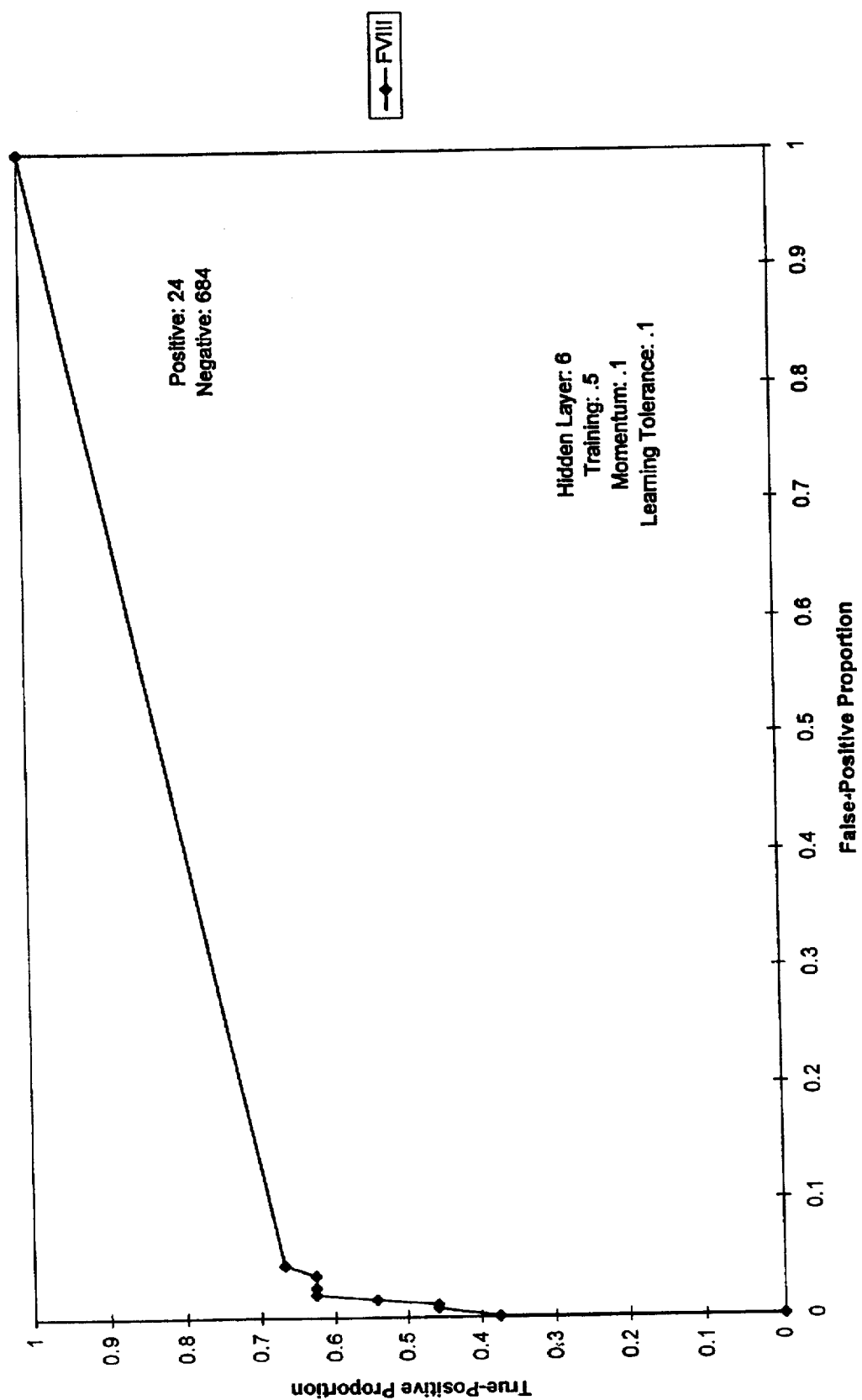
FIG. 10 is a receiver operator characteristic plot related to predicting an abnormality in relation to Factor VIII.
Figure 11:
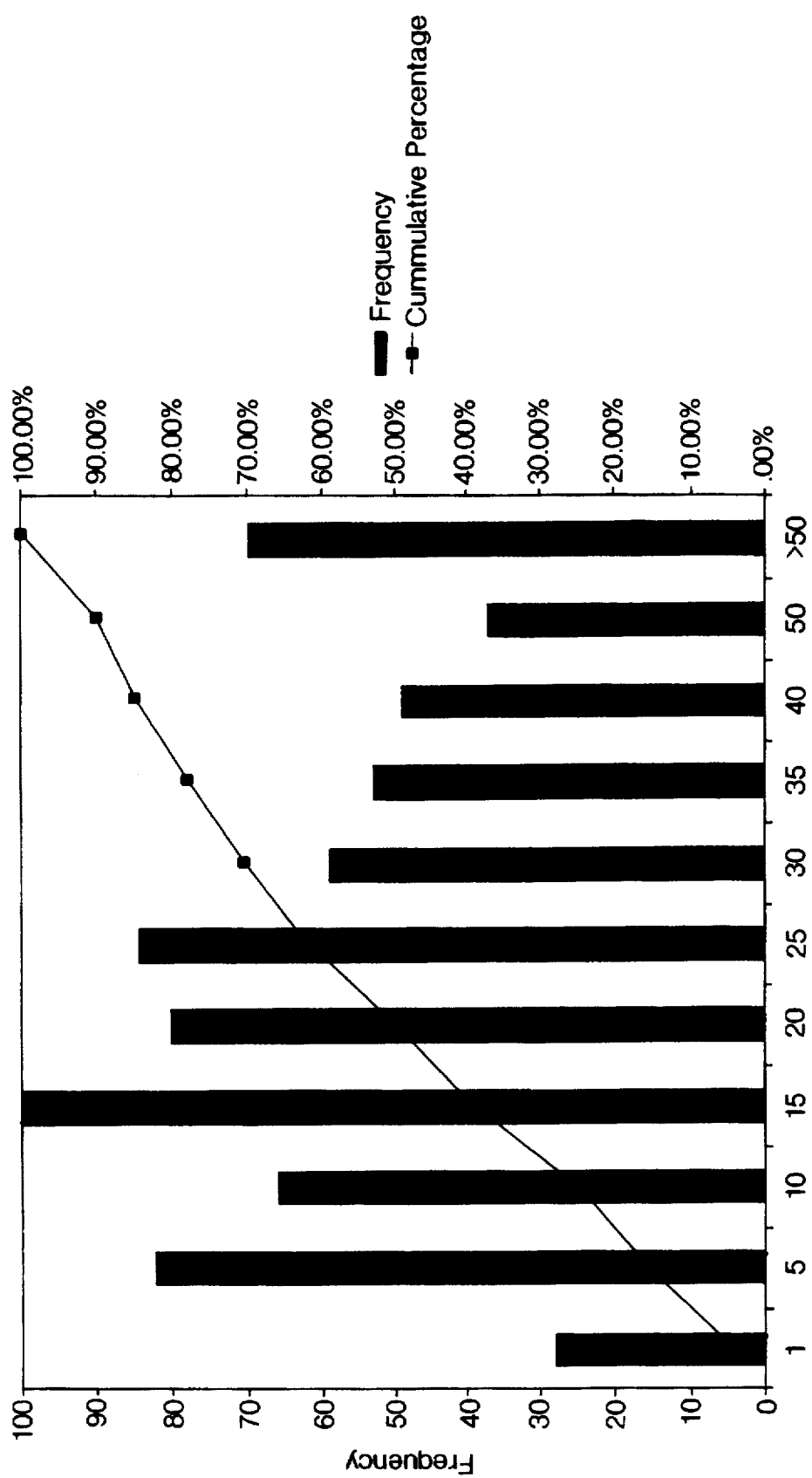
FIG. 11 is a graph demonstrating the ability to predict actual Factor VIII activity.

Similar tests were run as in Example 1. As can be seen in FIGS. 10 and 11, two training sessions were conducted for predicting a Factor VIII condition in an unknown sample. FIG. 10 is a receiver operator characteristic plot related to predicting an abnormality in relation to Factor VIII. In FIG. 10, everything below 30% activity was indicated as positive, and everything above 30% was indicated as negative. Cutoff values other than 30% could also be used. In this Example, the activity percentage has a known accuracy of approximately + or −10%. In FIG. 11, the actual percent activity was utilized as the output.

EXAMPLE 3

Factor X

Figure 12:
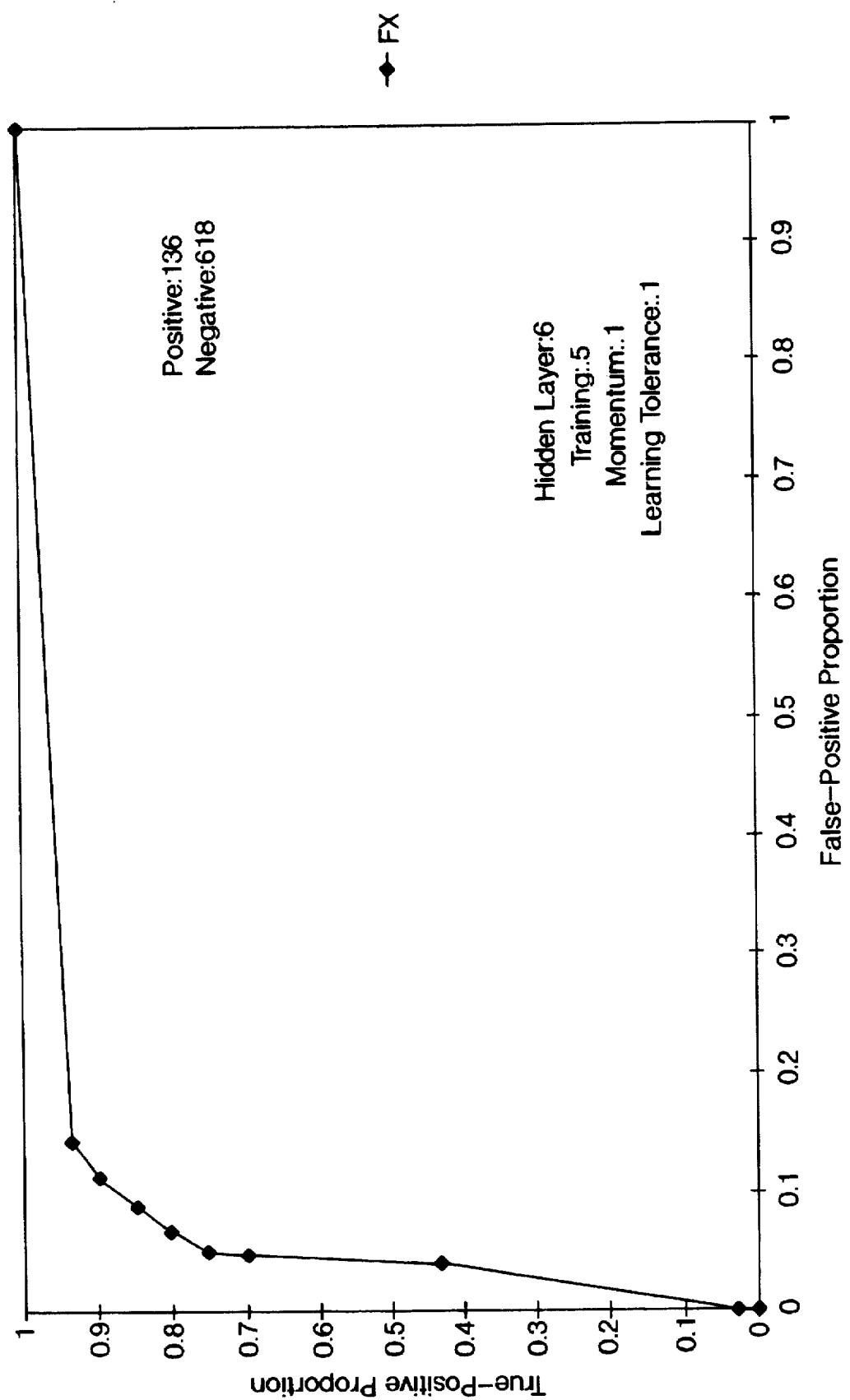
FIG. 12 is a receiver operator characteristic plot related to predicting an abnormality in relation to Factor X.

As can be seen in FIG. 12, the method of the present invention was run similar to that as in Example 2, where here an abnormality in Factor X concentration was predicted from unknown samples. Everything below 30% activity was indicated as positive, and everything above 30% was indicated as negative. Cutoff values other than 30% could also be used.

The results of the cross-validation sample sets throughout the experiments indicate that the sample size was sufficient for the network to generalize. While the random distribution of the training and cross-validation sets were held constant throughout the experiments presented, other distributions have been used. These distributions, while all yielding different results, still lead to the same general conclusion.

Many alternatives for or additions to the set of predictor variables were explored. This included coefficients of a curve fitted to the data profile, pattern recognition, and clot time-based parameters. Low order functions tend to lose information due to their poor fit, and high order functions tend to lose information in their multiple close solutions. Clot-based parameters, such as clot time, slope in the section prior to the initiation of clot formation, and afterwards, are often available, but not always (because in some samples, the clot time is not detectable). The successful results observed indicate that the set of predictor variables used are effective for predicting congenital or acquired imbalances or therapeutic conditions.

The optimization of the network learning algorithm's parameters made significant differences in its performance. In general, performance was best with low learning rates, high momentum rates, some small training error tolerance, and a hidden layer size approximately half of the size of the input layer.

It is to be understood that the invention described and illustrated herein is to be taken as a preferred example of the same, and that various changes in the method and apparatus of the invention may be resorted to, without departing from the spirit of the invention or scope of the claims.

We claim:

1. A method for predicting the presence of at least one congenital or acquired imbalance or therapeutic condition associated with thrombosis/hemostasis from at least one time-dependent measurement profile, comprising:

a) performing at least one time-dependent measurement on an unknown sample and measuring a respective property over time so as to derive a time-dependent measurement profile;

b) defining a set of a plurality of predictor variables which sufficiently define the data of the time-dependent measurement profile;

c) deriving a model that represents the relationship between the congenital or acquired imbalance or therapeutic condition, and the set of predictor variables; and d) utilizing the model of step c) to predict the existence of the congenital or acquired imbalance or therapeutic condition in the unknown sample;

wherein said set of predictor variables includes a plurality of: a minimum of the first derivative of the profile, a time index of the minimum of the first derivative, a minimum of the second derivative of the profile, a time index of the minimum of the second derivative, a maximum of the second derivative of the profile, a time index of the maximum of the second derivative, an overall change in the coagulation parameter during the time-dependent measurement on the unknown sample, a clotting time, a slope of the profile prior to clot formation, and a slope of the profile after clot formation.

2. A method according to claim 1, wherein said at least one time-dependent measurement profile is at least one optical profile.

3. A method according to claim 2, wherein said at least one optical profile is provided by an automated analyzer for thrombosis and hemostasis testing.

4. A method according to claim 2, wherein a plurality of optical measurements at one or more wavelengths are taken over time so as to derive said at least one optical profile, said optical measurements corresponding to changes in light scattering and/or light absorption in the unknown sample.

5. A method according to claim 2, wherein a plurality of optical measurements are taken over time so as to derive said at least one optical profile, and wherein said plurality of optical measurements are each normalized to a first optical measurement.

6. A method according to claim 3, wherein in step a) said at least one optical profile is provided automatically by said analyzer, whereby said unknown sample is automatically removed by an automated probe from a sample container to a test well, one or more reagents are automatically added to said test well so as to initiate said property changes within said sample, and the development of said property over time is automatically optically monitored so as to derive said optical data profile.

7. A method according to claim 6, wherein after step d), a predicted congenital or acquired imbalance or therapeutic condition is automatically stored in a memory of said automated analyzer and/or displayed on said automated analyzer.

8. A method according to claim 6, wherein in step d), one or more assays for confirming the existence of said congenital or acquired imbalance or therapeutic condition is automatically performed.

9. A method according to claim 8, wherein said one or more confirming assays are automatically ordered and performed on said analyzer, with results of said one or more assays being stored in a memory of said automated analyzer and/or displayed on said analyzer.

10. A method according to claim 1, further comprising: before step a), providing a set of data from known samples, which data is used in step c) for deriving said model.

11. A method according to claim 10, wherein said data from known samples is provided by performing a plurality of assays on said known samples.

12. A method according to claim 10, wherein said model of step c) is a neural network.

13. A method according to claim 1, wherein said relationship in step c) is determined via at least one automated algorithm.

14. A method according to claim 13, wherein said model is a multilayer perceptron, and wherein said at least one algorithm is a back propagation learning algorithm.

15. A method according to claim 1, wherein in step a), a plurality of time-dependent measurement profiles are derived for use in step b).

16. A method according to claim 15, wherein said plurality of time dependent measurement profiles includes at least two profiles from assays initiated with PT reagents, APTT reagents, fibrinogen reagents and TT reagents.

17. A method according to claim 1, wherein three or more of said predictor variables are within said set.

18. A method according to claim 17, wherein more than three of said predictor variables are within said set.

19. A method according to claim 1, wherein said unknown sample is a sample from a medical patient, and wherein in step d), both said model and additional patient medical data are utilized for predicting the existence of said congenital or acquired imbalance or therapeutic condition.

20. An apparatus for performing at least one time-dependent measurement on an unknown sample to derive at least one time-dependent measurement profile, and predicting the presence of at least one congenital or acquired imbalance or therapeutic condition associated with thrombosis/hemostasis from the at least one time-dependent measurement profile, comprising:

means for performing at least one time-dependent measurement on an unknown sample and measuring a respective property over time so as to derive a time-dependent measurement profile;

means for defining a set of a plurality of predictor variables which sufficiently define the data of the time-dependent measurement profile;

means for deriving a model that represents the relationship between the congenital or acquired imbalance or therapeutic condition, and the set of predictor variables; and means for utilizing the model of step c) to predict the existence of the congenital or acquired imbalance or therapeutic condition in the unknown sample;

wherein said set of predictor variables includes a plurality of: a minimum of the first derivative of the profile, a time index of the minimum of the first derivative, a minimum of the second derivative of the profile, a time index of the minimum of the second derivative, a maximum of the second derivative of the profile, a time index of the maximum of the second derivative, an overall change in the coagulation parameter during the time-dependent measurement on the unknown sample, a clotting time, a slope of the profile prior to clot information, and a slope of the profile after clot formation.

21. An apparatus according to claim 20, wherein said means for performing at least one time-dependent measurement comprises an optical system for performing at least one optical measurement over time and so as to derive an at least one optical profile.

22. An apparatus according to claim 21, wherein said optical system is part of an automated analyzer for thrombosis and hemostasis testing.

23. An apparatus according to claim 21, wherein said optical means comprises a means for performing a plurality of optical measurements at one or more wavelengths over time so as to derive said at least one optical profile, said optical measurements corresponding to changes in light scattering and/or light absorption in the unknown sample.

24. An apparatus according to claim 21, wherein in said optical system, a plurality of optical measurements are taken over time so as to derive said at least one optical profile, and wherein said plurality of optical measurements are each normalized to a first optical measurement.

25. An apparatus according to claim 22, which is an automated analyzer for thrombosis and hemostasis testing, and wherein said at least one optical profile is provided automatically by said analyzer, whereby said unknown sample is automatically removed by an automated probe from a sample container to a test well, one or more reagents are automatically added to said test well so as to initiate said property changes within said sample, and the development of said property over time is automatically optically monitored so as to derive said optical data profile.

26. An apparatus according to claim 25, further comprising at least one of a memory and a display wherein a predicted congenital or acquired imbalance or therapeutic condition is automatically stored in said memory of said automated analyzer and/or displayed on said display of said automated analyzer.

27. An apparatus according to claim 25, further comprising means for automatically performing one or more assays for confirming the existence of said congenital or acquired imbalance or therapeutic condition.

28. An apparatus according to claim 27, wherein said means for performing one or more confirming assays is an automatic performing means wherein said confirming assays are automatically ordered and performed on said analyzer, with results of said one or more assays being stored in a memory of said automated analyzer and/or displayed on a display of said analyzer.

29. An apparatus according to claim 20, further comprising means for providing a set of data from known samples, which data is used in step c) for deriving said model.

30. An apparatus, according to claim 29, wherein said data from known samples is provided by said means for performing a plurality of assays on said known samples.

31. An apparatus according to claim 29, wherein said means for deriving a model is a means for deriving a model by means of a neural network.

32. An apparatus according to claim 20, wherein said relationship determined by said deriving means comprises a means for determining said relationship via at least one automated algorithm.

33. An apparatus according to claim 32, wherein said model is a multilayer perceptron, and wherein said at least one algorithm is a back propagation learning algorithm.

34. An apparatus according to claim 20, wherein said means for performing at least one time-dependent measurement is capable of performing a plurality of time-dependent measurement profiles.

35. An apparatus according to claim 34, wherein said means for performing a plurality of time dependent measurement profiles includes a means for performing at least two profiles from assays initiated with PT reagents, APTT reagents, fibrinogen reagents and TT reagents.

36. An apparatus according to claim 20, wherein three or more of said predictor variables are within said set.

37. An apparatus according to claim 36, wherein more than three of said predictor variables are within said set.

38. An apparatus according to claim 20, wherein said unknown sample is a sample from a medical patient, and wherein said utilizing means comprising a means for utilizing both said model and additional patient medical data for predicting the existence of said congenital or acquired imbalance or therapeutic condition.

* * * * *

UNITED STATES PATENT AND TRADEMARK OFFICE
CERTIFICATE OF CORRECTION

PATENT NO. : 5,708,591
DATED : January 13, 1998
INVENTOR(S) : GIVENS

It is certified that error appears in the above-identified patent and that said Letters Patent is hereby corrected as shown below:

column 12, line 29, by deleting "information" and inserting -- formation --.

Signed and Sealed this

Fifteenth Day of May, 2001

Attest:

NICHOLAS P. GODICI

*Attesting Officer*   *Acting Director of the United States Patent and Trademark Office*